(12) United States Patent
Mereu et al.

(10) Patent No.: US 8,865,903 B2
(45) Date of Patent: Oct. 21, 2014

(54) CONTINUOUS PROCESS FOR THE ALKYLATION OF CYCLIC TERTIARY AMINES

(71) Applicant: Cerbios-Pharma SA, Barbengo/Lugano (CH)

(72) Inventors: Andrea Mereu, Grandate (IT); Moreno Morosoli, Tesserete (CH); Mauro Perseghini, Montagnola (CH); Alessandro Spreafico, Mandello del Lario (IT)

(73) Assignee: Cerbios-Pharma SA, Barbengo (Lugano) (CH)

( * ) Notice: Subject to any disclaimer, the term of this patent is extended or adjusted under 35 U.S.C. 154(b) by 81 days.

(21) Appl. No.: 13/683,448

(22) Filed: Nov. 21, 2012

(65) Prior Publication Data

US 2013/0165656 A1    Jun. 27, 2013

(30) Foreign Application Priority Data

Dec. 22, 2011  (EP) .................................. 11195419

(51) Int. Cl.
*C07D 215/38* (2006.01)
*C07D 207/12* (2006.01)
*C07D 491/04* (2006.01)
*C07D 451/00* (2006.01)
*C07D 451/12* (2006.01)
*C07D 209/94* (2006.01)

(52) U.S. Cl.
CPC ............ *C07D 451/00* (2013.01); *C07D 207/12* (2013.01); *C07D 491/04* (2013.01); *C07D 451/12* (2013.01); *C07D 209/94* (2013.01)
USPC ......................................................... 546/159

(58) Field of Classification Search
CPC ...................................................... C07D 247/02
USPC ......................................................... 546/159
See application file for complete search history.

(56) References Cited

FOREIGN PATENT DOCUMENTS

JP    2004-155669 A    6/2004
WO    03/053908 A1    7/2003

OTHER PUBLICATIONS

Burton, CA15-:515728, abstract only of e-EROS encyclopedia of Reagents for Organic synthesis, 2007.*

* cited by examiner

*Primary Examiner* — D M Seaman
(74) *Attorney, Agent, or Firm* — Lucas & Mercanti, LLP

(57) ABSTRACT

A continuous process for the alkylation of tertiary amines and, in particular, to a continuous process for the quaternization of cyclic tertiary amines useful for the preparation of cyclic quaternary ammonium salts with high purity is described.

20 Claims, No Drawings

CONTINUOUS PROCESS FOR THE ALKYLATION OF CYCLIC TERTIARY AMINES

CROSS-REFERENCE TO RELATED APPLICATION

This Application claims the benefit of priority from European Patent Application No. 11195419.4, filed Dec. 22, 2011, the contents of which are incorporated herein by reference.

FIELD OF THE INVENTION

The present invention relates to a continuous process for the alkylation of tertiary amines and, in particular, to a continuous process for the quaternization of cyclic tertiary amines useful for the preparation of cyclic quaternary ammonium salts with high purity.

BACKGROUND OF THE INVENTION

Several quaternary ammonium salts are known in the literature and useful in different technical fields. Their preparation usually includes the alkylation of tertiary amines as final step but most of these preparation methods require long reaction times.

For example, U.S. Pat. No. 2,956,062 describes batch synthetic methods for the alkylation of cyclic tertiary amines (N-substituted 3-pyrrolidinols) by reaction with an excess of an alkylating agent in a suitable solvent such as ether or ethyl acetate. The reaction requires several hours and even days to be completed.

U.S. Pat. No. 3,813,441 describes a continuous process for the production of quaternary aliphatic ammonium chlorides from aliphatic amines having a long chain by reaction with methyl chloride and an aqueous solution of an alkali hydroxide in a low-boiling solvent under pressure. The reaction by-product sodium chloride has to be removed continuously by filtration.

EP 0 288 857 describes a solvent-free process for the quaternization of tertiary amines with alkyl halides in a molar ratio ranging from 1:3 to 1:8 at elevated pressures (up to 27.5 bar).

U.S. Pat. No. 5,041,664 describes a continuous process for the quaternization of long chain tertiary amines with alkyl chlorides, heterogeneously catalyzed by a metal oxide.

U.S. Pat. No. 5,491,240 describes the preparation of quaternary ammonium compounds useful as fabric softeners and/or conditioning agents for the skin or hair. The preparation includes the quaternization of tertiary amines wherein the alkylating agent is added stage wise. The reaction time is about 10 hours.

EP 0 869 114 describes a batch process for the quaternization of ester-amines which requires reaction times of at least 24 hours. The resultant quaternary compounds are useful for softening applications.

WO 2011/091197 describes the preparation of quaternized N,N-dialkylaminoethyl(meth)acrylates useful as intermediates for cationic flocculant polymers. The preparation includes a two-phase process for the quaternization of N,N-dialkylaminoethyl(meth)acrylates wherein the phase containing the product is continuously removed from the tank reactor.

Some cyclic quaternary ammonium salts such as, for example, tiotropium bromide (chemical name: 1α,2β,4β,7β)-7-[(hydroxy-di-2-thienylacetyl)oxy]-9,9-dimethyl-3-oxa-9-azonia-tricyclo[3.3.1.0$^{2,4}$]nonane bromide) of formula

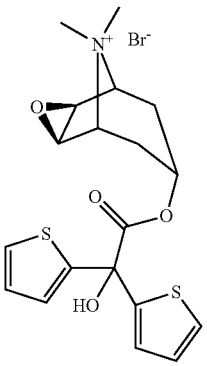 [SMILES: C[N+]1(C)C2CC(OC(=O)C(O)(c3cccs3)c3cccs3)CC1[C@@H]1O[C@H]21 ; [Br-]]

marketed under the trademark Spiriva®,
glycopyrronium bromide (chemical name: 3-(2-cyclopentyl-2-hydroxy-2-phenylacetoxy)-1,1-dimethylpyrrolidinium bromide) of formula

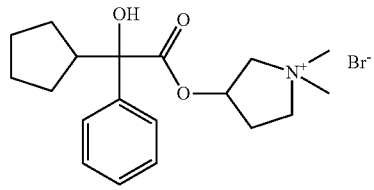 [SMILES: C[N+]1(C)CCC(OC(=O)C(O)(c2ccccc2)C2CCCC2)C1 ; [Br-]]

marketed under the trademark Robinul®, and ipratropium bromide (chemical name: [8-methyl-8-(1-methylethyl)-8-azoniabicyclo[3.2.1]oct-3-yl]-3-hydroxy-2-phenyl-propanoate) of formula

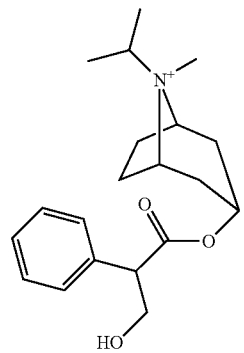 [SMILES: CC(C)[N+]1(C)C2CCC1CC(OC(=O)C(CO)c1ccccc1)C2]

marketed under the trademark Atrovent®, are known anticholinergic drugs with different applications, mainly for the treatment of chronic obstructive pulmonary disease (COPD).

Their preparation usually includes the alkylation of the corresponding cyclic tertiary amines as a final step but most of these preparation methods require long reaction times and further purification to achieve a suitable pharmaceutical grade.

For example, U.S. Pat. No. 5,610,163 describes the preparation of tiotropium bromide and its analogs by reaction of the corresponding cyclic tertiary amines dissolved in methylene chloride/acetonitrile with a solution of methyl bromide in acetonitrile at room temperature for 24 hours.

There is still the need of an efficient improved process, particularly of an efficient continuous process for the preparation of cyclic quaternary ammonium compounds. We have now found a method for the continuous alkylation of cyclic tertiary amines, particularly useful for the production of cyclic quaternary ammonium compounds with high purity as required for pharmaceutical use, which is more efficient than the known quaternization processes.

DETAILED DESCRIPTION OF THE INVENTION

An object of the present invention is to provide a method for the continuous alkylation of cyclic tertiary amine. The method comprises:

continuously feeding a solution of a cyclic tertiary amine in a suitable solvent or mixture of solvents and an alkylating agent, optionally dissolved in a suitable solvent or mixture of solvents, into a continuous-flow reactor;

maintaining the temperature within the range of 20-140° C.;

collecting the solution containing the pure quaternary cyclic ammonium compound; and isolating the pure quaternary cyclic ammonium compound.

The method of the present invention allows one to directly obtain the quaternary cyclic ammonium compound with high purity without the need of any further purification step. Moreover, the method offers several additional advantages over the known methods such as better reaction control, better temperature control of the reaction and easy scale up for larger output.

For the purpose of the present application, cyclic tertiary amine and cyclic quaternary ammonium compounds are compounds of general formula (I) or (II)

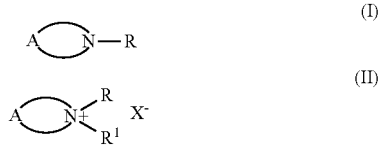

respectively,
wherein
R is a linear or branched $C_1$-$C_{12}$ alkyl group;
$R^1$ is a linear or branched $C_1$-$C_3$ alkyl group;
X is a halogen atom or a carbonate, sulfate or triflate; and
A is a radical forming optionally substituted monocyclic, bicyclic or tricyclic ring with the nitrogen atom.

In the compounds of formula (I) and (II), preferred meanings of R are $C_1$-$C_4$ alkyl groups such as methyl, ethyl, propyl, isopropyl, butyl, isobutyl and t.butyl; with methyl and isopropyl being particularly preferred.

In the compounds of formula (II), preferred meanings of $R^1$ are methyl, ethyl, propyl, and isopropyl, with methyl being particularly preferred.

In the compounds of formula (I) and (II), said rings are selected among optionally substituted monocyclic rings having from 4 to 7 atoms, optionally including 1 or 2 heteroatoms selected from among N, O and S, in addition to the nitrogen atom to which they are linked; optionally substituted bicyclic rings having from 6 to 9 atoms, optionally including 1 or 2 heteroatoms selected from among N, O and S, in addition to the nitrogen atom to which they are linked; and optionally substituted tricyclic rings having from 8 to 12 atoms, optionally including 1 or 2 heteroatoms selected from among N, O and S, in addition to the nitrogen atom to which they are linked.

Examples of particularly preferred monocyclic, bicyclic and tricyclic ring are the rings of formulae

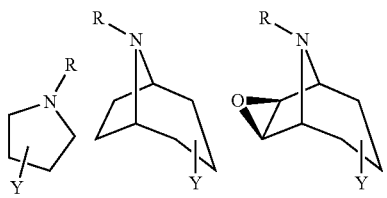

and the corresponding quaternary ammonium salts

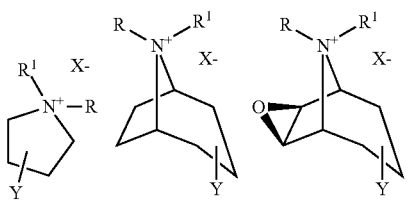

wherein R, $R^1$ and X have the above mentioned meanings and Y is a substituent selected from among (cyclo)alkyl, aryl, heteroaryl, arylalkyl, heteroarylalkyl, (cyclo)alkoxy, aryloxy, heteroaryloxy, (cyclo)alkylcarbonyl, arylcarbonyl, heteroarylcarbonyl, (cyclo)alkylcarbonyloxy, arylcarbonyloxy, heteroarylcarbonyloxy, arylalkylcarbonyloxy, and heteroarylalkylcarbonyloxy.

In a particularly preferred embodiment of the present invention, Y is selected from among (cyclo)alkylcarbonyloxy, arylalkylcarbonyloxy and heteroarylalkylcarbonyloxy groups.

Examples of particularly preferred meanings of the substituent Y are the groups of formula:

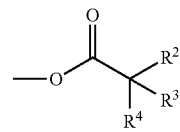

wherein $R^2$, $R^3$ and $R^4$, the same or different, are hydrogen, hydroxy, hydroxyalkyl, preferably hydroxymethyl, phenyl, cycloalkyl, preferably cyclopentyl, and heteroaryl, preferably thienyl.

Specific examples are

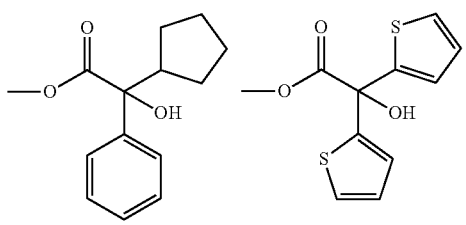

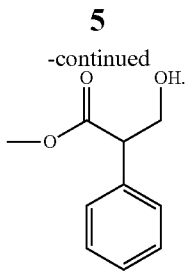

The alkylating agent useful in the method according to the present invention is a compound of formula $R^1X$ wherein $R^1$ and X have the above mentioned meanings.

Preferably the alkylating agent is a compound of formula $R^1X$ wherein X is a halogen atom selected among Cl, Br and I, still more preferably X is Br.

Examples of alkylating agents useful in the method according to the present invention are methyl chloride, methyl bromide, methyl iodide, ethyl chloride, ethyl bromide, ethyl iodide, n-propyl chloride, n-propyl bromide, n-propyl iodide, isopropyl chloride, isopropyl bromide, and isopropyl iodide.

Methyl chloride, methyl bromide and methyl iodide are particularly preferred, with methyl bromide being still more preferred.

The method of the present invention is characterized by the use of a suitable solvent or mixture of solvents to dissolve the cyclic tertiary amine and optionally also the alkylating agent.

The selection of the solvent is critical to achieve the desired results, that is high conversion and high purity.

The Applicant has carried out several experiments to maximize conversion while maintaining a high level of purity in the final compound and found that better results are achieved by using polar aprotic solvents selected from among amides, nitriles and sulphoxides, such as for example acetonitrile, dimethylformamide, dimethylacetamide, N-methylpyrrolidone and dimethylsulphoxide.

The polar aprotic solvent is used for the preparation of the solution of the cyclic tertiary amine to be quaternized according to the process of the present invention.

The alkylating agent can be used neat or as a solution in a suitable solvent.

Said solvent can be the same solvent used to dissolve the cyclic tertiary amine or a different solvent.

When the alkylating agent is used as a solution in the method of the present invention, preferably the solvent is a polar aprotic solvent different from the solvent used for the dissolution of the amine.

Acetonitrile is particularly preferred for the preparation of the solution of the alkylating agent to be used in the method according to the present invention.

Particularly preferred solvents for the dissolution of the cyclic tertiary amine are dimethylacetamide, dimethylsulphoxide and N-methylpyrrolidone.

The combination of N-methylpyrrolidone for the dissolution of the cyclic tertiary amine and of acetonitrile for the dissolution of the alkylating agent is still more preferred.

The solution of the cyclic tertiary amine and the alkylating agent as neat or as a solution can be introduced into the continuous-flow reactor separately or, as an alternative, the solution the cyclic tertiary amine and the alkylating agent as neat or as a solution can be pre-mixed before the introduction into the continuous-flow reactor.

The reaction temperature ranges from 20 to 200° C., and is preferably from 40 to 85° C.

The flow rate has to be properly adjusted in order to obtain an optimal residence time of the reaction mixture in the continuous flow reactor with the aim of completing the reaction.

Flow and pressure ranges used are characteristics of the reaction model. For example, in the case of Corning Advanced Flow G1, typically the flow is in the range of 1 to 30 g/min and the pressure is in the range from 1 to 20 bar.

The method according to the present invention is particularly useful for the preparation of anticholinergic drugs such as tiotropium bromide, glycopyrronium bromide and ipratropium bromide.

In a particularly preferred embodiment, the method according to the present invention is useful for the preparation of tiotropium bromide.

The present invention is now illustrated without limiting it by the following examples.

Comparative Example 1

Tiotropium Bromide Batch Synthesis

In a 250 ml flask under nitrogen, N-demethyltiotropium (10.0 g) was dissolved in N-methylpyrrolidone (33 ml) at room temperature. A 1:1 (w/w) mixture methylbromide/acetonitrile (25 g) was added. After 22 hours under stirring at room temperature, the white precipitate was filtered, washed with acetone, and dried.
HPLC purity: 99.66%

Example 2

Tiotropium Bromide Via Flow Chemistry With Liquid Methyl Bromide

A solution of N-demethyltiotropium (12 g) in acetonitrile (139.4 ml) and dichloromethane (180 ml) was injected into a continuous-flow reactor at a rate of 10 g/min. Liquid methyl bromide was injected at a rate of 0.5 g/min. The reactor temperature was 40° C.

The solution coming out from the continuous-flow reactor was collected and stirred overnight at room temperature. The precipitate was filtered, washed with dichloromethane, and dried under reduced pressure.

Example 3

Tiotropium Bromide Via Flow Chemistry With Methyl Bromide As Solution, Premixed

A 1:1 (w/w) mixture methylbromide/acetonitrile (15 g) was added to a solution of N-demethyltiotropium (6.0 g) in N-methylpyrrolidone (20 ml). The solution was injected into a continuous-flow reactor at a rate of 10 g/min. The reactor temperature was 80° C. The solution coming out from the continuous-flow reactor was collected, cooled to room temperature, then to 0° C. Acetone (100 ml) was added. The resulting suspension was stirred for an additional hour, then stored at 0-5° C. overnight. The product was filtered, washed twice with acetone, and dried under reduced pressure.
HPLC purity: 99.98%

$^1$H-NMR (300 MHz, $d_6$-DMSO): 7.52 (dd, J=5.0 Hz, 1.1, 2H), 7.41 (s, 1H), 7.13 (dd, J=3.6, 1.1 Hz, 2H), 7.01 (dd, J=5.0, 3.7 Hz, 2H), 5.12 (t, J=5.8 Hz, 1H), 4.13 (bd, J=5.8 Hz, 2H), 3.50 (s, 2H), 3.25 (s, 3H), 3.05 (s, 3H), 1.93 (s, 1H), 1.87 (s, 1H).

$^{13}$C-NMR (75.5 MHz, $d_6$-DMSO): 170.2, 147.1, 127.3, 126.7, 126.3, 76.8, 65.0, 64.2, 56.5, 54.1, 47.6, 28.7.

X-ray spectrum is identical with the x-ray spectrum of tiotropium bromide obtained according to the procedure described in U.S. Pat. No. 5,610,163.

Example 4

The procedure of examples 2 and 3 has been repeated with different solvents or mixture of solvents.
The results are summarized in the following table.

TABLE 1

| Solvent amine/MeBr | Pressure | Temperature | Conversion | Purity |
|---|---|---|---|---|
| $CH_2Cl_2$ + MeCN/— | 0.35 bar (liquid) | 41° C. | 17% | n.d. |
| $CH_2Cl_2$/MeCN | 12.3 bar | 70° C. | 25% | 99.1% |
| MeOH/MeCN | 15.6 bar | 81° C. | 61% | 73.9% |
| MeOH/MeCN | 3.4 bar | 80° C. | 84% | n.d. |
| DMF/MeCN | 10.6 bar | 81° C. | 97% | n.d. |
| DMA/MeCN | 10.6 bar | 81° C. | 97% | 99.95% |
| DMSO/MeCN | 10.8 bar | 81° C. | 94% | 98.20% |
| NMP/MeCN | 10.3 bar | 81° C. | 99.7% | 99.98% |

The obtained results show that dichloromethane is a poor solvent for the final product, which may precipitate in the continuous-flow reactor and obstruct the channels. The replacement of dichloromethane with methanol allows to increase the temperature but conversion is rather low. The use of polar aprotic solvents selected among amides, nitriles and sulphoxides, according to the present invention, results in very high conversions. Moreover, the process is very clean and the final product can be isolated with a very high purity fulfilling the requirement of pharmaceutical applications with no need of further purification.

Example 5

Preparation of Glycopyrronium Bromide

Glycopyrronium bromide was prepared by working in a similar way as described in example 3.
$^1$H-NMR (300 MHz, $D_2O$): 7.71-7.63 (m, 2H), 7.53-7.38 (m, 3H), 5.54 (s, 1H), 3.92-3.68 (m, 2H), 3.67-3.49 (m, 2H), 3.23-3.14 (m, 1H), 3.22 (s, 3Ha), 3.18 (s, 3Hb), 3.06 (s, 3Ha), 2.90 (s, 3Hb), 2.84-2.64 (m, 1H), 2.45-2.31 (m, 1Hb), 2.23-2.09 (m, 1Ha), 1.81-1.46 (m, 8H), 1.34-1.20 (m, 1H).
13C-NMR (75.5 MHz, $D_2O$): 174.4, 140.6+140.5 (1 $C_{a+b}$), 128.7 (2C), 128.3, 126.2+126.0 (2 $C_{a+b}$), 80.7+80.5 (1 $C_{a+b}$), 74.0, 70.1, 64.8, 53.5, 52.9, 44.9+44.7 (1 $C_{a+b}$), 29.9+29.7 (1 $C_{a+b}$), 26.6+26.5 (1 $C_{a+b}$), 26.1+26.0 (2 $C_{a+b}$), 25.8+25.7 (1 $C_{a+b}$).
a=(R,S)/(S,R)
b=(S,S)/(R,R)

Example 6

Preparation of Ipratropium Bromide

Ipratropium bromide was prepared by working in a similar way as described in example 3.
$^1$H-NMR (300 MHz, $D_2O$): 7.41-7.25 (m, 5H), 5.09-5.02 (m, 1H), 4.19-4.07 (m, 1H), 3.97-3.87 (m, 2H), 3.87-3.79 (m, 1H), 3.76-3.68 (m, 1H), 2.71 (s, 3H), 2.61-2.41 (m, 2H), 2.30-1.91 (m, 3H), 1.71 (d, J=17 Hz, 1H).
$^{13}$C-NMR (75.5 MHz, $D_2O$): 173.0, 135.2, 129.2 (2C), 128.3 (2C), 128.2, 65.5, 65.4, 64.1, 62.1, 55.5, 53.5, 39.0, 30.7 (2C), 24.4, 24.1, 15.5 (2C).

The invention claimed is:

1. A method for the continuous alkylation of cyclic tertiary amines comprising:
continuously feeding a solution of a cyclic tertiary amine in a suitable solvent or mixture of solvents and of an alkylating agent into a continuous-flow reactor, wherein said suitable solvents or mixture of solvents are polar aprotic solvents selected from the group consisting of amides, nitriles and sulphoxides;
maintaining the temperature within the range of 20-200° C.;
collecting the solution containing the pure quaternary cyclic ammonium compound; and
isolating the pure quaternary cyclic ammonium compound;
wherein
said cyclic tertiary amines and quaternary cyclic quaternary ammonium compounds are compounds of general formulae

respectively,
wherein
R is a linear or branched $C_1$-$C_{12}$ alkyl group;
$R^1$ is linear or branched $C_1$-$C_3$ alkyl group;
X is a halogen atom or a carbonate, sulfate or triflate; and
A is a radical forming, optionally substituted monocyclic, bicyclic or tricyclic ring with the nitrogen atom, said ring being selected among from optionally substituted monocyclic rings having from 4 to 7 atoms, optionally including 1 or 2 heteroatoms selected among from N, O and S, in addition to the nitrogen atom to which they are linked; optionally substituted bicyclic rings having from 6 to 9 atoms, optionally including 1 or 2 heteroatoms selected among from N, O and S, in addition to the nitrogen atom to which they are linked; and optionally substituted tricyclic ring having from 8 to 12 atoms, optionally including 1 or 2 heteroatoms selected among from N, O and S, in addition to the nitrogen atom to which they are linked.

2. A method according to claim 1 wherein R is a $C_1$-$C_4$ alkyl group.

3. A method according to claim 2 wherein R is methyl or isopropyl.

4. A method according to claim 1 wherein $R^1$ is methyl.

5. A method according to claim 1 wherein said monocyclic, bicyclic and tricyclic rings are the rings of formula

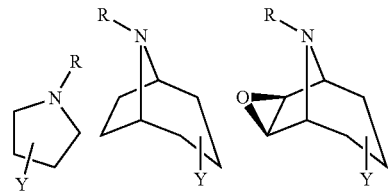

and the corresponding quaternary ammonium salts

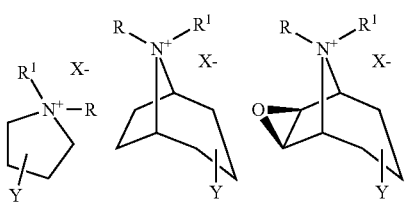

wherein

R, $R^1$ and X have the above defined meanings and

Y is a substituent selected from the group consisting of (cyclo)alkyl, aryl, heteroaryl, arylalkyl, heteroarylalkyl, (cyclo)alkoxy, aryloxy, heteroaryloxy, (cyclo)alkylcarbonyl, arylcarbonyl, heteroarylcarbonyl, (cyclo)alkylcarbonyloxy, arylcarbonyloxy, heteroarylcarbonyloxy, arylalkylcarbonyloxy, and heteroarylalkylcarbonyloxy.

6. A method according to claim 5 wherein Y is selected from the group consisting of (cyclo)alkylcarbonyloxy, arylalkylcarbonyloxy and heteroarylalkylcarbonyloxy.

7. A method according to claim 6 wherein Y is a group of formula:

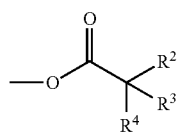

wherein $R^2$, $R^3$ and $R^4$, are the same or different, and are independently selected from among hydrogen, hydroxy, hydroxyalkyl, preferably hydroxymethyl, phenyl, cycloalkyl, preferably cyclopentyl, and heteroaryl, preferably thienyl.

8. A method according to claim 1 wherein the alkylating agent is a compound of formula $R^1X$ wherein $R^1$ is linear or branched $C_1$-$C_3$ alkyl group; and X is a halogen atom or a carbonate, sulfate or triflate.

9. A method according to claim 8 wherein the alkylating agent is a compound of formula $R^1X$ wherein X is a halogen atom selected from the group consisting of Cl, Br and I.

10. A method according to claim 9 wherein the alkylating agent is selected from the group consisting of methyl chloride, methyl bromide, methyl iodide, ethyl chloride, ethyl bromide, ethyl iodide, n-propyl chloride, n-propyl bromide, n-propyl iodide, isopropyl chloride, isopropyl bromide, and isopropyl iodide.

11. A method according to claim 10 wherein the alkylating agent is methyl bromide.

12. A method according to claim 1 wherein said polar aprotic solvent are selected from the group consisting of acetonitrile, dimethylformamide, dimethylacetamide, N-methylpyrrolidone and dimethylsulphoxide.

13. A method according to claim 1 wherein the alkylating agent is introduced into the continuous-flow reactor neat.

14. A method according to claim 1 wherein the alkylating agent is introduced into the continuous-flow reactor as a solution, optionally pre-mixed with the solution of the cyclic tertiary amine.

15. A method according to claim 14 wherein the solvent for the preparation of the solution of the alkylating agent is acetonitrile.

16. A method according to claim 1 wherein the solvent for the dissolution of the cyclic tertiary amine is selected from the group consisting of dimethylacetamide, dimethylsulphoxide and N-methylpyrrolidone.

17. A method according to claim 16 wherein the solvent is N-methylpyrrolidone.

18. A method according to claim 1 wherein the temperature ranges from 20 to 200° C., preferably from 40 to 85° C.

19. A method according to claim 1 for the preparation of tiotropium bromide, glycopyrronium bromide and ipratropium bromide.

20. A method of claim 1 wherein the isolated quaternary cyclic ammonium compound has a purity of at least 99.95%.

* * * * *